United States Patent [19]
Wilks, Jr.

[11] Patent Number: 5,125,742
[45] Date of Patent: Jun. 30, 1992

[54] LONG PATH GAS ABSORPTION CELL

[75] Inventor: Paul A. Wilks, Jr., Darien, Conn.

[73] Assignee: General Analysis Corporation, South Norwalk, Conn.

[21] Appl. No.: 558,076

[22] Filed: Jul. 25, 1990

[51] Int. Cl.⁵ .............................................. G01N 21/03
[52] U.S. Cl. .................................... 356/246; 356/440
[58] Field of Search ............... 356/236, 246, 437, 448; 250/343, 373, 576

[56] References Cited

U.S. PATENT DOCUMENTS

| | | | |
|---|---|---|---|
| 3,287,557 | 11/1966 | Bartz | 250/343 |
| 3,431,424 | 3/1969 | Allen | 356/246 |
| 3,436,159 | 4/1969 | Harrick et al. | 356/51 |
| 3,556,659 | 1/1971 | Haws | 356/246 |
| 3,591,287 | 7/1971 | Hannis | 356/244 |
| 3,728,540 | 4/1973 | Todd et al. | 250/51 |
| 3,792,272 | 2/1974 | Harte et al. | 250/437 |
| 4,726,680 | 2/1988 | Allington | 356/246 |
| 4,818,882 | 4/1989 | Nexo et al. | 250/343 |

FOREIGN PATENT DOCUMENTS

| | | | |
|---|---|---|---|
| 282636 | 11/1988 | Japan | 356/440 |
| 2042205 | 9/1980 | United Kingdom . | |
| 2105058 | 3/1983 | United Kingdom . | |
| 2117920 | 10/1983 | United Kingdom . | |

*Primary Examiner*—Richard A. Rosenberger
*Attorney, Agent, or Firm*—F. Eugene Davis, IV

[57] ABSTRACT

The multi-pass, multi-reflection (MIR) cell used for spectrographic analysis, in a spectrophotometer, for example, is a right circular cylinder having flat end plates perpendicular to its axis. The interior of the cylinder is appropriately coated to reflect the radiation employed and small transparent windows are provided on axis at each end plate. Appropriate input and output tubing is provided. The cell is not much longer than it is in diameter and may have a diameter greater than its length, thus it is either drum or disk-shaped in contrast to the long light pipes of the prior art. The cell is preferably illuminated by a cone of radiation, such as that employed in multiple internal reflection instruments, for liquid analysis employing frustrated total internal reflection in circular rod. A spectrophotometer employing the cell is disclosed.

15 Claims, 4 Drawing Sheets

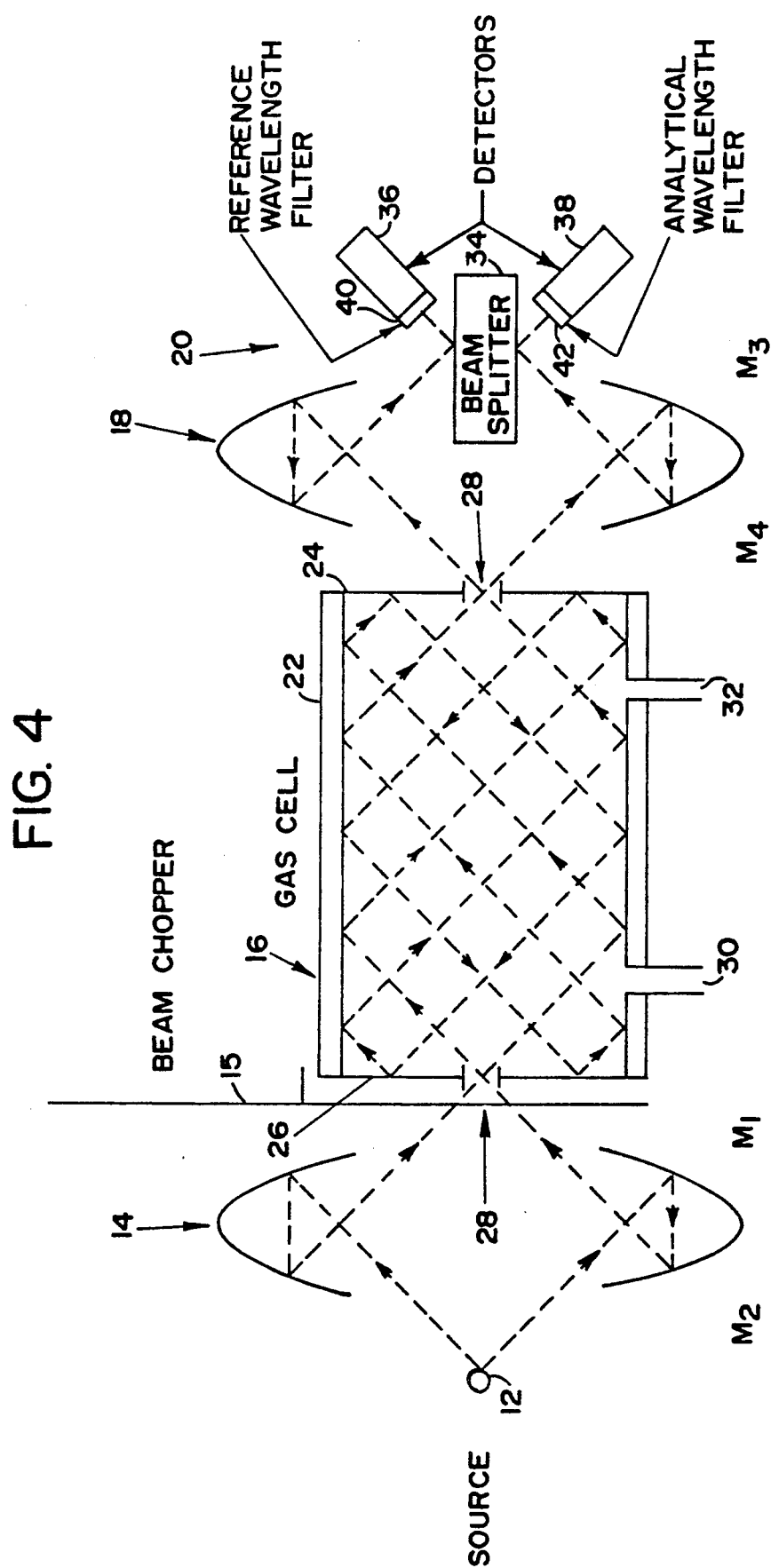

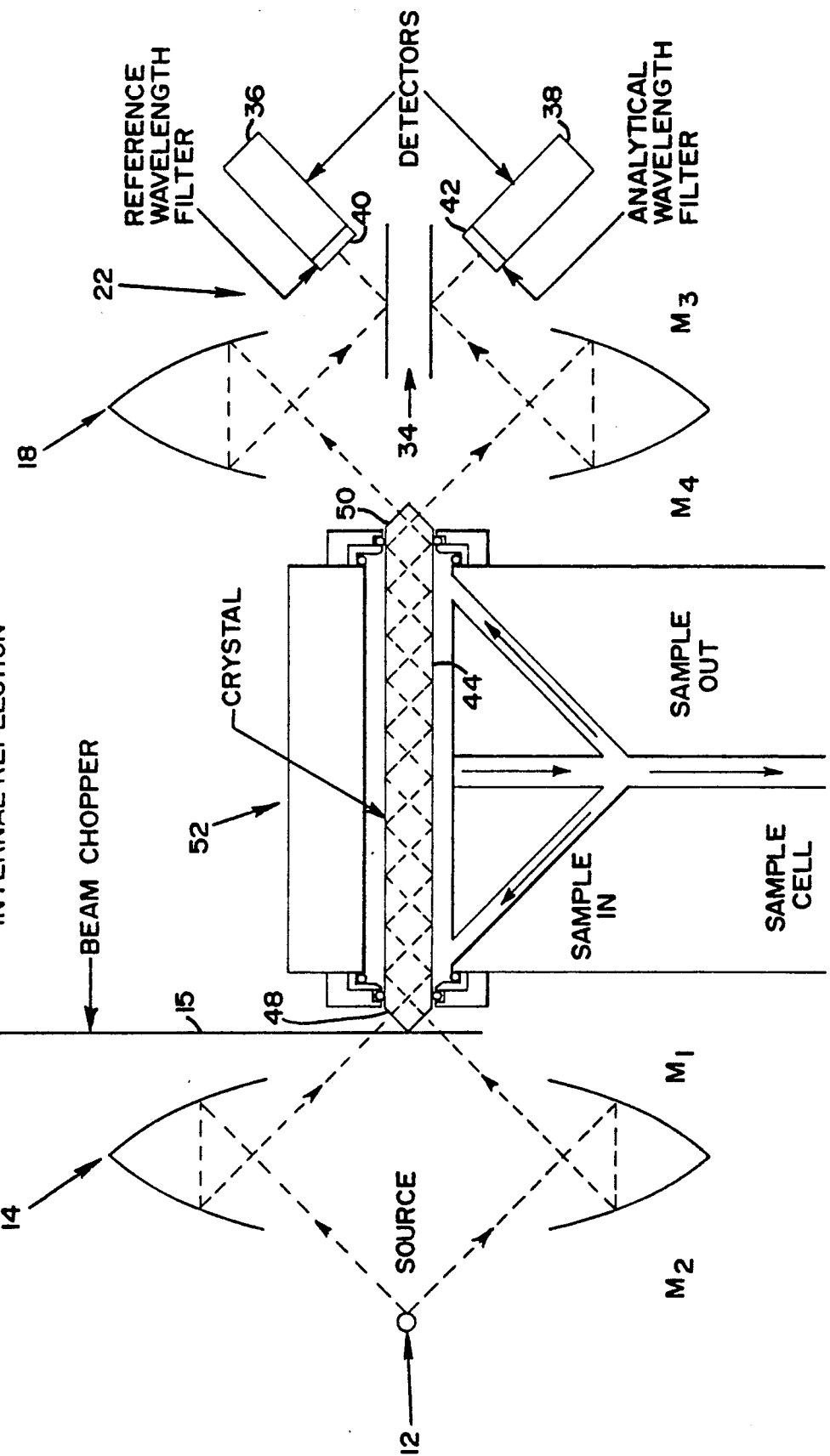

LONG PATH GAS ABSORPTION CELL

BACKGROUND OF THE INVENTION

This invention relates to long path gas absorption cells for spectrographic analysis, particularly those that can be utilized in existing spectrophotometers employing frustrated total internal reflection in elongated rods having conical end faces. Instruments of this type are disclosed in my prior U.S. Pat. No. 3,370,502, Issued: Feb. 27, 1968, entitled FRUSTRATED MULTIPLE INTERNAL REFLECTION ROD WITH VARIABLE LENGTH FLUID CONTAINING ENCLOSURE MEANS; and U.S. Pat. No. 3,460,893, Issued: Aug. 12, 1969, entitled APPARATUS FOR ANALYZING A CONTINUOUSLY MOVING STRIP BY MEANS OF ATENUATED TOTAL INTERNAL REFLECTION; and, in particular, in my British Patent No. 2,105,058, granted Jan. 8, 1986 entitled FRUSTRATED MULTIPLE TOTAL INTERNAL REFLECTION ABSORPTION SPECTROPHOTOMETER. Another form of optical system, in which my new gas cell may be employed, is a spectrophotometer employing reflaxicon optics and also using a rod with conical end faces disclosed in U.S. Pat. No. 4,595,833 of Donald W. Sting, Issued: Jun. 17, 1986 for MULTIPLE INTERNAL REFLECTION CELL OPTICAL SYSTEM FOR USE IN INFRA-RED SPECTROPHOTOMETERY OF LIQUID AND FLUIDIZED SAMPLES.

Instruments according to both of these latter patents, are available from Spectra-Tech, Inc., Stamford, Conn. U.S.A. under the Trademark The Circle ™.

Instruments according to my above-identified British Patent, are available from General Analysis Corporation, South Norwalk, Conn., U.S.A. under the Trademark LAN ™.

The gas cell of the present invention is designed to be directly substituted for the conical end face frustrated total internal reflection liquid sampling rod and cell used in the above-identified instruments.

As these instruments employ cells of relatively short lengths, in the order of 1 to 3 inches, traditional gas cells employing light pipes—that is very long, thin cylinders—do not provide sufficient absorption in these instruments for many applications

OBJECTS OF THE INVENTION

It is therefore an object of the invention to provide a long path gas absorption cell for spectrographic analysis which itself is of short length.

Another object of the invention is to provide such a gas cell for use in existing spectrophotometers employing circularly symmetric optical systems.

Another object of the invention is to provide such a gas cell which may be directly substituted in existing instruments employing a multiple internal reflection rod having conical end faces.

Other objects of the invention include providing such a gas absorpiion cell that is compact, simple to fabricate, and inexpensive.

Other objects of the invention will in part be obvious and will in part appear hereinafter.

The invention accordingly comprises the features of construction, combinations of elements and arrangements of parts which will be exemplified in the constructions hereinafter set forth. The scope of the invention is indicated in the claims.

SUMMARY OF THE INVENTION

Such a gas cell must be able to accept the wide angle of beam convergence and short focal length of, for example, the LAN ™ optical system—which is approximately f 0.7.

The concept is simple: The cell body is a cylinder with the inner surface coated with a highly reflective coating. The cell ends are infrared transmitting windows, the inner surfaces of which are also coated with a highly reflective coating except for circular uncoated areas in their centers. The windows are flat. Another way of fabricating the cell ends is to start with a reflecting disc. Cut a hole in it and cement in a small IR transmitting window.

Radiation from the source is focussed at a steep angle of convergence through the small, uncoated aperture in the entrance window. The beam of energy will expand rapidly beyond the focal point until it strikes the cylinder wall which will then reflect it to another focal point. It will expand again to be re-reflected by the cylinder and so forth until it reaches the flat end window which is distanced from the entrance window so that it is not an exact whole number multiple of the focal length. A small amount of the energy will escape at this point but the bulk of it will be reflected back through the cylinder toward the entrance window where it will be reflected back again.

Eventually, all of the energy except for reflection losses will escape from the source end where it will eventually return to the source or from the exit end where it will be collected and focussed on the detector.

The effective path length is a function of the diameter and length of the cylinder (the larger the longer the path) and the size of the entrance and exit apertures.

Since the incoming energy is a bundle of rays of different angles, they will make a variety of passes through the cell but the average path will be close to that of the central ray.

From a number of central ray traces, it is apparent that the ratio of diameter to cell length determines the effective pathlength.

In a spectrophotometer, according to the invention, light arrives at the entrance window as conically converging rays, the principal rays of which form a conical sheet. The axis of the conical sheet is coincident with the optical axis and the axis of the gas absorption cell according to the invention. A preferred angle of the apex of this cone is 90° as this provides retroreflection of radiation to the source which is reflected at the entrance window.

I have found that a cell according to my invention, 1.8" in diameter and 2.8" in length has an effective path length of approximately 20 centimeters and that a gas cell, according to my invention, having a 2.8" diameter and 3.1"in length has an approximately 50 centimeter effective path length. These dimensions being the internal dimensions of the cell. The apperature windows are ¼" in diameter.

My cell may be characterized as having walls forming an enclosure about a central axis with generally flat end faces having small windows. The dimensions of the cell are chosen such that light focussed on a window is multiply internally reflected and makes a multiple pass through the cell. This occurs when the length of the cell is not a whole number multiple of the focal length of the radiation focussed on the entrance window.

BRIEF DESCRIPTION OF THE DRAWINGS

For a fuller understanding of the nature and objects of the invention, reference should be had to the following detailed description, taken in connection with the accompanying drawings, in which:

FIG. 4 is an optical schematic diagram of the spectrophotometer of FIG. 1 employing my gas cell; and FIG. 5 is an optical schematic diagram of the spectrophotometer of FIG. 1 utilizing a circular rod having conical end faces in a frustrated multiple internal reflection fluid analyzing cell.

The same reference characters refer to the same elements throughout the several views of the drawings.

BEST MODE FOR CARRYING OUT THE INVENTION

Figure 1:
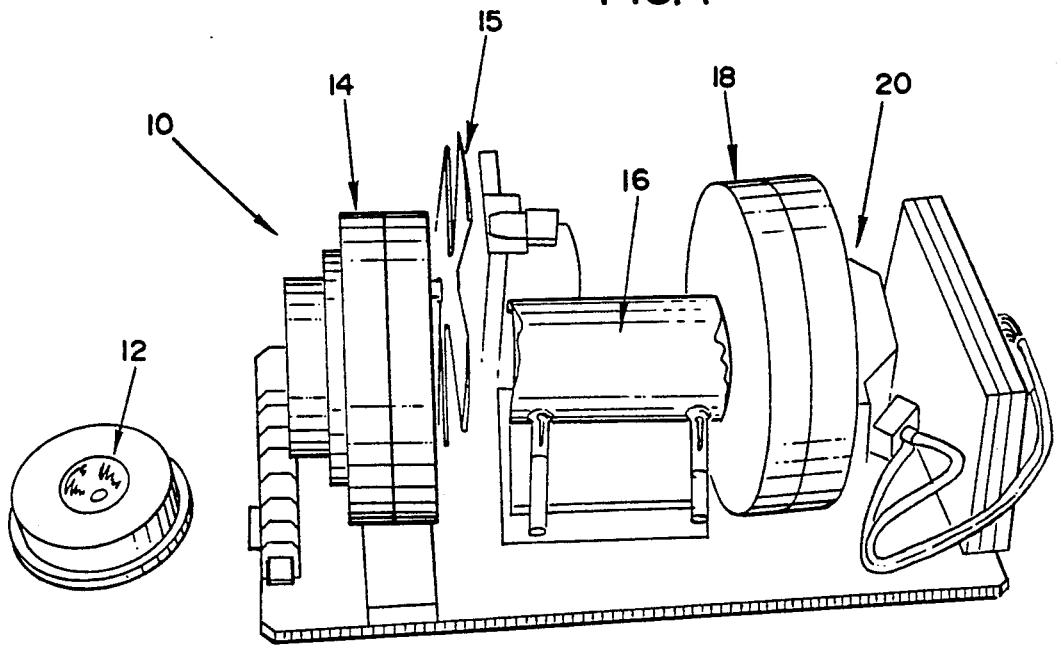
FIG. 1 is a photograph of a spectrophotometer employing the long path gas absorption cell of my invention.

Now referring to FIG. 1, a spectrophotometer (10), according to the invention, comprises a hot wire source (12), two-mirror optics generally indicated at (14), a chopper (15), my new gas cell (16) collecting optics generally indicated at (18) which is preferrably identical to the optics (14), and radiation analyzing detectors generally indicated at (20).

Figure 2:
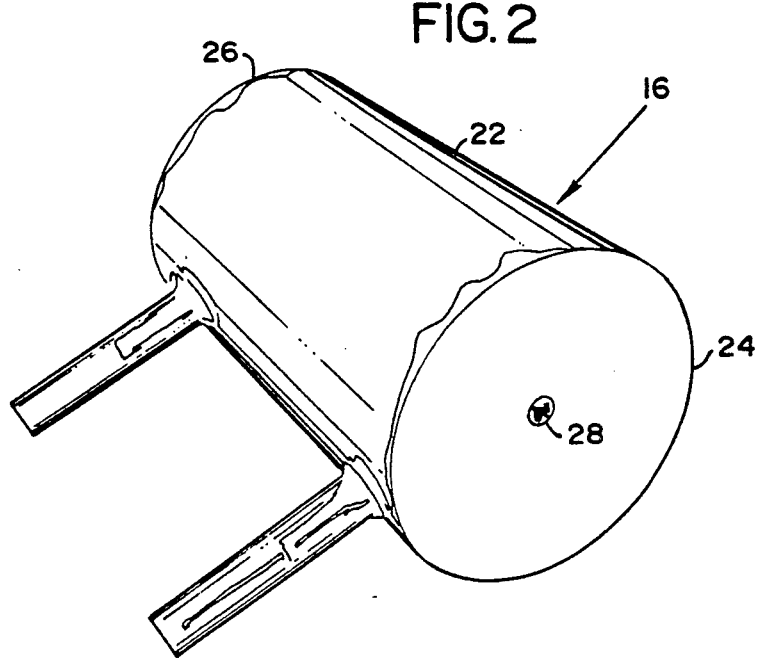
FIG. 2 is a photograph of the cell of FIG. 1.

As shown in FIG. 2, the gas cell (16) may be formed of a glass right circular cylinder (22) having end plates (24 and 26). The end plates (24 and 26) may be of glass with small radiation transmitting windows (28), except for the windows (28), the interior of the cell (16) is preferrably gold-plated for infra-red analysis. Other high reflecting coatings may be employed at different wavelengths. The end faces may also be constructed of flat plates of infra-red transmitting material having their interior surface entirely coated accept for the windows (28), which may be for example zinc selenide. The windows are the same size as the image of the source (12) focussed on them.

Figure 3:
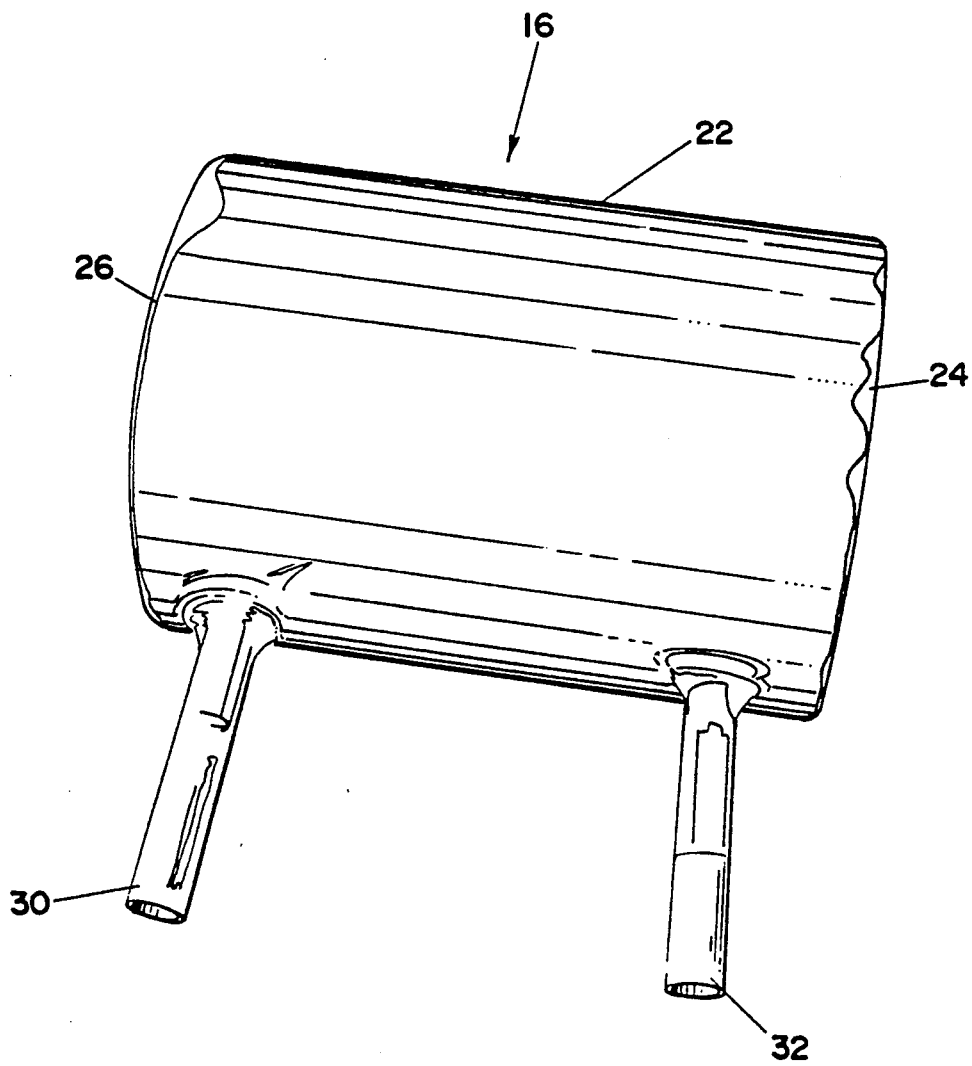
FIG. 3 is another photograph of the cell of FIG. 1.

Now referring to FIG. 3, the gas cell (16) is provided with an inlet pipe (30) and an outlet pipe (32) for passing a gas through the cell.

Now referring to FIG. 4, it will be seen how the central rays forming a conical sheet formed by the mirrors (14), enter the entrance aperture (28) on the left are multiply reflected within the gas cell and because the gas cell is not an exact interval of the focal length are reflected at the end face (24) back to the end face (26), and then again through the cell and exit at the exit aperture (28) on the right. The central rays exit in the same conical sheet form as they enter the cell and are focused by collection optics (18) which is identical to optics (14), divided by a beam splitter (34) and focussed on at least, two detectors (36 and 38). Detector (36) is the reference detector and has a reference wavelength filter (40) and detector (38) is the analytical wavelength detector and has an analytical wavelength filter (42).

Thus, it will be seen how the gas cell (16) according to my invention can be utilized in existing instruments, such as that, shown in FIG. 5 employing a right circular rod (44) having conical end faces (48 and 50) in a fluid analysis cell generally indicated at (52).

It will thus be seen that the objects set forth above, among those made apparent from the preceding description, are efficiently attained and, since certain changes may be made in the above constructions and elements without departing from the scope of the invention, it is intended that all matter contained in the above description shown in the accompanying drawings shall be interpreted as illustrative and not in a limiting sense.

Those skilled in the art will understand that the gas cells according to my invention may be employed by other wavelengths than the infra-red, may be used for any fluid, and that other optical systems for providing highly convergent illumination of the cells may be employed.

It is also to be understood that the following claims are intended to cover all of the generic and specific features of the invention herein described, and all statements of the scope of the invention which, as a matter of language, might be said to fall therebetween.

Having described my invention what I claim as new and desire to secure by Letters Patent is:

1. A fluid sample absorption cell comprising:
   A. an internally reflecting generally cylindrical side wall; and,
   B. generally flat end faces substantially perpendicular to the axis of said side wall, said end faces being internally reflecting except for small windows in said faces on said axis, said side wall and said end faces adapted to contain a fluid sample.

2. The cell of claim 1 wherein said side wall forms a right circular cylinder.

3. The cell of claim 1 wherein the length of said cell is no more than 5 times the diameter thereof.

4. A spectrographic instrument employing the cell of claim 1 and further comprising:
   C. an optical system having a focal length for focussing radiation from a source on to one of said windows; and
   wherein the distance between said end faces is not a whole number multiple of said focal length.

5. The instrument of claim 4 wherein said optical system focuses said radiation in a conical sheet of central rays.

6. The instrument of claim 5 wherein the apex angle of said cone is substantially 90°.

7. A spectrographic instrument as defined in claim 4, and;
   D. a detector for receiving radiation exiting from said second window 8. A fluid sample absorption cell comprising:
   A. internally reflecting side walls having opposed generally parallel surfaces surrounding a central axis parallel thereto; and,
   B. internally reflecting generally flat end faces perpendicular to said axis and having small windows to radiation along said central axis;
   wherein the spacing between said side walls and the spacing between said end walls is chosen such that radiation focussed on one of said windows will be multiply internally reflected by both said walls and said end faces and multiply pass through the cell, and said side walls and said end faces are adapted to contain a fluid sample.

9. The absorption cell of claim 8 wherein the distance between said end faces is not a whole number multiple of the focal length of said focussed radiation.

10. The cell of claim 7 wherein said side wall forms a right circular cylinder.

11. The cell of claim 7 wherein the length of said cell is no more than 5 times the diameter thereof.

12. A spectrographic instrument employing the cell of claim 7 and further comprising:
C. an optical system having a focal length for focussing radiation from a source on to one of said windows; and
wherein the distance between said end faces is not a whole number multiple of said focal length.

13. The instrument of claim 12 wherein said optical system focuses said radiation in a conical sheet of central rays.

14. The instrument of claim 13 wherein the apex angle of said cone is substantially 90°.

15. A spectrographic instrument as defined in claim 12, and;
D. a detector for receiving radiation exiting from said second window.

* * * * *